(12) United States Patent
Preiss et al.

(10) Patent No.: US 6,414,176 B2
(45) Date of Patent: Jul. 2, 2002

(54) PREPARATION OF VINYLSILANES

(75) Inventors: Thomas Preiss, Weisenheim am Sand; Holger Friedrich, Bobenheim-Roxheim; Jochem Henkelmann, Mannheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/901,891

(22) Filed: Jul. 11, 2001

(30) Foreign Application Priority Data

Jul. 18, 2000 (DE) .......................... 100 34 894

(51) Int. Cl.[7] .................................. C07F 7/08
(52) U.S. Cl. ...................................... 556/479
(58) Field of Search .......................... 536/479

(56) References Cited

U.S. PATENT DOCUMENTS

| | | | |
|---|---|---|---|
| 2,637,738 A | | 5/1953 | Wanger |
| 2,823,218 A | | 2/1958 | Speier |
| 4,579,965 A | * | 4/1986 | Kanner et al. ............... 556/479 |
| 5,041,595 A | * | 8/1991 | Yang et al. .................. 556/479 |
| 5,563,287 A | * | 10/1996 | Roy ............................ 556/479 |
| 5,565,596 A | | 10/1996 | Roy |
| 5,567,848 A | * | 10/1996 | Roy ............................ 556/479 |
| 6,111,126 A | * | 8/2000 | Tachikawa et al. ......... 556/479 |

FOREIGN PATENT DOCUMENTS

EP 409 141 1/1991

* cited by examiner

Primary Examiner—Paul F. Shaver
(74) Attorney, Agent, or Firm—Keil & Weinkauf

(57) ABSTRACT

In the process for the preparation of vinylsilanes by reacting acetylenic hydrocarbons with silanes which have at least one silicon-bonded hydrogen atom in the liquid phase in the presence of a catalyst, the silane is added to the liquid phase. In particular, the reaction is carried out at superatmospheric pressure, and the spent acetylenic hydrocarbon is replenished during the reaction while maintaining a pressure which is constant during the entire reaction.

10 Claims, No Drawings

PREPARATION OF VINYLSILANES

The present invention relates to a process for the preparation of vinylsilanes.

Vinylsilanes are industrially useful products which are used, for example, as adhesion promoters and as comonomers in moisture-curable polyolefins.

The synthesis of vinylsilanes by reacting acetylenic hydrocarbons with silicon compounds which contain at least one hydrogen atom (hydrosilylation) is known from the literature.

However, the yields of the desired vinylsilanes are frequently moderate in the processes known from the literature, since the reaction results in undesirable byproducts, in particular coupling products, which are formed by further hydrosilylation of the desired vinylsilanes.

U.S. Pat. No. 2,823,218 relates to a process for reacting silicon compounds which have a silicon-hydrogen bond with aliphatically unsaturated compounds, improved yields of the corresponding products and reduced yields of the byproducts being obtained at low reaction temperatures. The reaction is carried out by adding a mixture of a silicon compound and an aliphatically unsaturated hydrocarbon to an inert solvent containing chloroplatinic acid as a catalyst. In example 21, the reaction of acetylene with triacetoxysilane is disclosed. Acetylene is added to a mixture of triacetoxysilane and chloroplatinic acid in isopropanol. The product obtained is vinyltriacetoxy-silane. However, no yield is stated.

U.S. Pat. No. 2,637,738 relates to the reaction of silanes with unsaturated aliphatic compounds, such as acetylene and ethylene. The catalyst, platinum on active carbon, and the corresponding silane are initially taken and are reacted with acetylene or ethylene, preferably under superatmospheric pressure. According to Table 1, in which the results of the investigation of the reaction of acetylene with trichlorosilane are presented, 75% of the desired vinyl compound and 25% of the undesired coupling product are obtained with the use of 5% of platinum on powdered active carbon as a catalyst.

U.S. Pat. No. 5,565,596 relates to the reaction of silanes, in particular di- or trichlorosilanes, with alkynes over a platinum catalyst. In order to reduce the formation of bissilylated adducts of the alkynes, a catalyst modifier is added. The reaction is carried out after addition of the silane as a mixture with the alkyne to an inert solvent containing the platinum catalyst and the catalyst modifier. In the examples, the weight ratio of the desired vinylsilane to bissilylated derivatives is stated. The absolute yield of the desired vinylsilane is not stated in the examples.

EP-A 0 409 141 relates to the preparation of alkenylsilanes by reacting a gaseous acetylenic hydrocarbon with a gaseous silane which has a silicon-hydrogen bond in the presence of a hydrosilylation catalyst. The yield of desired alkenylsilane is said to be maximized and the yield of undesired byproducts is said to be minimized. At the same time, the dangers which occur when working with gaseous acetylenic hydrocarbons are said to be reduced. The reaction is carried out by feeding a gaseous mixture containing an acetylenic hydrocarbon and a silane to a reaction medium in the form of a dilute, mobile liquid film. This liquid film contains the desired alkenylsilane prepared during the reaction and a dissolved hydrosilylation catalyst and, if required, an organic solvent. The ratio of the acetylenic hydrocarbon to the silane is >1 and the reaction pressure is from atmospheric pressure to 2 atm. Table 1 shows the ratios of desired vinylsilane to undesired coupling product. However, an absolute yield of vinylsilane is not stated.

The problems associated with the formation of coupling products in the reaction of silanes which have at least one silicon-hydrogen bond with acetylenic hydrocarbons is thus known from the prior art. According to the prior art, the reaction is carried out either by adding a mixture of silane and unsaturated hydrocarbon to a solution containing a catalyst or by adding a gaseous acetylenic hydrocarbon to a mixture of silane, catalyst and, if required, solvent.

It is an object of the present invention to provide a process for the preparation of vinylsilanes, in which a very high conversion with high selectivities is to be achieved in combination with a very high space-time yield.

We have found that this object is achieved by a process for the preparation of vinylsilanes by reacting acetylenic hydrocarbons with silanes which have at least one silicon-bonded hydrogen atom in the liquid phase in the presence of a catalyst.

In the novel process, the silane is added to the liquid phase containing the acetylenic hydrocarbon and the catalyst.

This process differs from the processes known from the prior art in that the silane is added to a mixture of acetylenic hydrocarbon and catalyst. As a result of the controlled addition of the silane, an exact temperature program in the reactor is ensured. Furthermore, it is possible in this way to prevent a local excess of silane and to avoid coupling products.

An acetylenic hydrocarbon of the formula $R^1C \equiv CH$, where $R^1$ is alkyl of 1 to 4 carbon atoms or hydrogen, is preferably used. A gaseous acetylenic hydrocarbon is thus preferably used. The gaseous acetylenic hydrocarbon acetylene ($R^1 = H$) is particularly preferred.

Preferred silanes are those of the formula $HSiR^2{}_nX_{3-n}$, where $R^2$ is alkyl or halogenated alkyl, X is a halide or alkoxy and n is from 0 to 3. $R^2$ is preferably alkyl or halogenated alkyl of 1 to 6, preferably 1 to 3, carbon atoms. X is preferably chloride or alkoxy $OR^3$, where $R^3$ can be alkyl or aryl. $R^3$ is preferably a $C_1$- to $C_6$-alkyl or a $C_6$- to $C_{12}$-aryl radical. $R^3$ is particularly preferably $C_1$- to $C_3$-alkyl, very particularly preferably methyl. If X is a halide, n is preferably from 0 to 2. If X is alkoxy, n is preferably from 0 to 1, particularly preferably 0. Accordingly, trialkoxysilanes of the formula

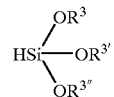

where $R^3$, $R^{3'}$ and $R^{3''}$, independently of one another, have the meanings stated for $R^3$, are very particularly preferably used.

In a preferred embodiment, the novel process is carried out at superatmospheric pressure. The pressure is in general from 5 to 30, preferably from 15 to 25, particularly preferably from 15 to 20, bar. The reaction is preferably carried out at constant pressure, the gaseous acetylenic hydrocarbon being replenished at the rate at which it is consumed, so that a constant pressure is maintained.

The catalyst used in the novel process is preferably a homogeneously dissolved catalyst. Suitable catalysts are those selected from Pt or Pd catalysts. A homogeneously dissolved platinum catalyst is particularly preferably used. A catalyst of the formula $Pt(0)L_m$, where m is from 2 to 4 and L is any desired suitable ligand, for example tetramethyldivinyl-disiloxane, is very particularly preferably used. Tetramethyldidivinylsiloxaneplatinum is very particularly preferably used as the catalyst. By operating under superatmospheric pressure in a homogeneously catalyzed reaction, it is possible to achieve high space-time yields which in general are from 50 to 2 000 g/lh, depending on the corresponding product.

The homogeneous catalyst is generally used in a concentration of from 1 to 1 000 ppm, preferably from 1 to 100 ppm, particularly preferably from 1 to 40 ppm, based on the silane used.

The reaction is preferably carried out in an inert high-boiling solvent, selected from aliphatic and aromatic hydrocarbons and mixtures of different hydrocarbons and high-boiling esters and ethers. High-boiling aromatic hydrocarbons, such as xylene, are particularly preferred.

In a preferred embodiment of the novel process, a silane is reacted with a gaseous acetylenic hydrocarbon, preferably acetylene. An inert high-boiling solvent, for example xylene, is initially taken and a platinum catalyst is homogeneously dissolved therein. The gaseous acetylenic hydrocarbon is added until a pressure of 20 bar (18 bar partial pressure of the acetylenic hydrocarbon) is reached. The silane to be reacted is then pumped in. The duration for which the silane is pumped in is dependent on the batch size and on the reactor geometry. In this reaction, the gaseous acetylenic hydrocarbon is replenished at the rate at which it is consumed, so that the reaction is carried out at constant pressure.

The hydrosilylation of acetylenic hydrocarbons can thus be carried out under mild reaction conditions at low temperatures. In general, temperatures of from 0 to 80° C., preferably from 0 to 60° C., particularly preferably from 0 to 40° C., are customary.

The novel process is preferably carried out in such a way that the temperature variation in the reactor during the reaction after heating up to the reaction temperature is in general not more than 10° C., preferably not more than 5° C., particularly preferably not more than 2° C.

By means of this procedure, high selectivities of in general from 90 to >99%, preferably from 95 to >99%, particularly preferably from 98 to >99%, are obtained. Undesired byproducts and secondary reactions are avoided or suppressed by means of this procedure.

The yield of vinylsilane is in general from 89 to 99.9%, preferably from 94 to 99.5%, based on the silane used.

The novel process can be carried out in all reactors suitable for this reaction. The process is preferably carried out in a tubular reactor, stirred reactor or loop reactor. A reaction in a loop reactor is particularly preferred.

The examples which follow additionally illustrate the invention.

EXAMPLES

COMPARATIVE EXAMPLE 600 g of xylene, 200 g of trimethoxysilane and 1 g of tetramethyldivinyldisiloxaneplatinum solution in xylene (150 ppm) were initially taken in a 2.5 l autoclave. The reactor was then provided with an inert atmosphere by means of 2 bar nitrogen and was heated to 40° C. while stirring. After the reaction temperature had been reached, the pressure was increased to 20 bar by forcing in acetylene. In the course of one hour, the internal temperature increased to 50° C. and was then reduced to 40° C. by cooling. After 2 hours at 20 bar, the autoclave was cooled to room temperature and let down. Starting material was no longer detectable in the reaction discharge. The yield of trimethoxyvinylsilane was 47.7%. 1,2-(Trimethoxy)ethylsilane and 1,1-(trimethoxy)ethylsilane were detectable as byproducts.

Example

(According to the Invention)

647 g of xylene and 0.1 g of tetramethyldivinyl-disiloxaneplatinum solution in xylene (20 ppm) were initially taken in a 2.5 l autoclave. The reactor was then provided with an inert atmosphere by means of 2 bar nitrogen and the pressure was increased to 20 bar by forcing in acetylene. In the course of 30 minutes, 140 g of trimethoxysilane were pumped in. During this time, the reactor pressure was kept at 20 bar with acetylene. After 2 hours at 20 bar and 40° C., the autoclave was cooled to room temperature and let down. Starting material was no longer detectable in the reaction discharge. The yield of trimethoxyvinylsilane was 99.3%.

We claim:

1. A process for the preparation of vinylsilanes by reacting acetylenic hydrocarbons with silanes which have at least one silicon-bonded hydrogen atom in the liquid phase in the presence of a catalyst, wherein the silane is added to the liquid phase containing the acetylenic hydrocarbon and the catalyst.

2. A process as claimed in claim 1, wherein an acetylenic hydrocarbon of the formula $R^1C\equiv CH$, where $R^1$ is alkyl of 1 to 4 carbon atoms or hydrogen, is used.

3. A process as claimed in claim 2, wherein acetylene ($R^1$=H) is used.

4. A process as claimed in claim 1, wherein silanes of the formula $HSiR^2_nX_{3-n}$, where $R^2$ is alkyl or halogenated alkyl, X is a halide or alkoxy and n is from 0 to 3, are used.

5. A process as claimed in claim 4, wherein a silane of the formula

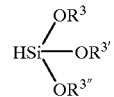

where $R^3$, $R^{3'}$ and $R^{3''}$, independently of one another, are alkyl, aryl or alkenyl, is used.

6. A process as claimed in claim 1, wherein the reaction is carried out at superatmospheric pressure.

7. A process as claimed in claim 6, wherein the pressure is from 15 to 25 bar.

8. A process as claimed in claim 6, wherein the consumed acetylenic hydrocarbon is replenished during the reaction while maintaining a pressure which is constant during the entire reaction.

9. A process as claimed in claim 1, wherein the catalyst is a homogeneously dissolved catalyst.

10. A process as claimed in claim 9, wherein a catalyst of the formula $Pt(0)L_m$, where m is from 2 to 4 and L is any desired suitable ligand, is used.

* * * * *